US010548531B2

(12) United States Patent
Park et al.

(10) Patent No.: US 10,548,531 B2
(45) Date of Patent: Feb. 4, 2020

(54) FOLDABLE-CASE-INTEGRATED-TYPE MULTI-DEVICE

(71) Applicant: INDUSTRY FOUNDATION OF CHONNAM NATIONAL UNIVERSITY, Gwangju (KR)

(72) Inventors: Kyung Eun Park, Seoul (KR); Jong Jin Park, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 157 days.

(21) Appl. No.: 15/126,400

(22) PCT Filed: Mar. 16, 2015

(86) PCT No.: PCT/KR2015/002531
§ 371 (c)(1),
(2) Date: Sep. 15, 2016

(87) PCT Pub. No.: WO2015/142014
PCT Pub. Date: Sep. 24, 2015

(65) Prior Publication Data
US 2017/0079592 A1    Mar. 23, 2017

(30) Foreign Application Priority Data

Mar. 19, 2014  (KR) .................. 10-2014-0032208

(51) Int. Cl.
*A61B 5/00* (2006.01)
*A45C 11/00* (2006.01)
(Continued)

(52) U.S. Cl.
CPC ............ *A61B 5/6898* (2013.01); *A45C 11/00* (2013.01); *A61B 5/0205* (2013.01);
(Continued)

(58) Field of Classification Search
CPC ................ A61B 10/0051; A61B 5/157; G01N 27/3272; G01N 27/3273; G01N 33/48785; G01N 27/307
See application file for complete search history.

(56) References Cited

U.S. PATENT DOCUMENTS 5,687,732 A * 11/1997 Inagaki .............. A61B 5/02233
600/485
6,699,188 B2 * 3/2004 Wessel ............... A61B 5/04325
600/300

(Continued)

FOREIGN PATENT DOCUMENTS

KR    20050025554    3/2005
KR    20050103355    10/2005
(Continued)

OTHER PUBLICATIONS

International Search Report, issued in the corresponding International Application No. PCT/KR2015/002531, dated Apr. 29, 2015, 4 pages.

*Primary Examiner* — Michael W Kahelin
(74) *Attorney, Agent, or Firm* — Hamre, Schumann, Mueller & Larson, P.C.

(57) ABSTRACT

The present invention relates to a foldable case-integrated multi-device and a health management system using the same, in which health management and life management functions are implemented by introducing various sensors into a foldable case for a communication device. According to the present invention, a sensor module configured to measure biometric information is contained in a foldable case, and power supply, data processing and analysis, and display are implemented using internal components of the communication device, thereby providing a cutting-edge (Continued)

health care function while maintaining a communication device in a light, thin, short and small form.

14 Claims, 7 Drawing Sheets

(51) Int. Cl.
    *H04B 1/3888*     (2015.01)
    *A61B 5/0205*     (2006.01)
    *H04M 1/02*     (2006.01)
    *G06F 19/00*     (2018.01)
    *H04M 1/725*     (2006.01)
    *G16H 40/63*     (2018.01)
    *A61B 5/0402*     (2006.01)
    *A61B 5/08*     (2006.01)
    *A61B 5/145*     (2006.01)
    *A61B 5/021*     (2006.01)

(52) U.S. Cl.
    CPC .......... *A61B 5/0402* (2013.01); *A61B 5/0816* (2013.01); *A61B 5/14532* (2013.01); *A61B 5/14535* (2013.01); *A61B 5/14542* (2013.01); *A61B 5/14546* (2013.01); *A61B 5/4343* (2013.01); *G06F 19/00* (2013.01); *G06F 19/3418* (2013.01); *G16H 40/63* (2018.01); *H04B 1/3888* (2013.01); *H04M 1/0214* (2013.01); *H04M 1/72527* (2013.01); *A45C 2011/002* (2013.01); *A61B 5/02108* (2013.01); *A61B 2560/0242* (2013.01); *A61B 2560/0406* (2013.01); *A61B 2560/0443* (2013.01); *A61B 2562/0219* (2013.01); *A61B 2562/0295* (2013.01); *A61B 2562/18* (2013.01); *H04M 2250/12* (2013.01)

(56) References Cited

U.S. PATENT DOCUMENTS 8,150,485 B2 *   4/2012   Lee ..................... G06F 1/1626
                                                                                 379/428.01
8,211,364 B2 *   7/2012   Drucker ............ A61B 5/14532
                                                                                     422/68.1

FOREIGN PATENT DOCUMENTS

KR       20080073571         8/2008
KR       20130017105        2/2013

* cited by examiner

FOLDABLE-CASE-INTEGRATED-TYPE MULTI-DEVICE

TECHNICAL FIELD

The present invention relates to a foldable case-integrated multi-device, and more particularly to a foldable case-integrated multi-device in which health management and life management functions are implemented by introducing various sensors into a foldable case for a communication device, such as a smartphone or the like.

BACKGROUND ART

Communication devices are intelligent terminals in which computer-supported functions, such as an Internet communication function, an information search function, etc., have been added to conventional mobile phones. Based on applications, various functions are being added to the functions of communication devices.

Communication devices are equipped with a mobile instant messenger function adapted to transmit messages, photos, moving images, voices, contact information, etc. to counterparts, a camera function, a navigation function, a Digital Multimedia Broadcasting (DMB) function, a multimedia player function adapted to play back MPEG Audio Layer-3 (MP3) data and digital moving images, an additional security function using biometric information such as an iris identification function or a fingerprint identification function, etc. It is expected that the functions of more digital devices will be converged via application programs using applications.

Meanwhile, since interest in medical welfare and well-being is increasingly growing due to an increase in the level of income, the focus of a medical field is shifting from the treatment of disease and illness to health management and preventive health care. In line with this trend, recently, there has been actively conducted research and development of home health care systems in which medical welfare is combined with a ubiquitous concept, thereby significantly reducing the temporal and spatial limitations of health diagnosis and health management.

With the development of technology for the integration and miniaturization of electronic devices, there have been developed portable measuring devices capable of measuring the blood sugar level, blood pressure, electrocardiogram or the like of an individual without requiring a visit to a hospital. However, these portable measuring devices merely measure biometric information, but do not provide a comprehensive function for preventing and managing diseases by storing the measured data and integrating the stored data.

Accordingly, the development of self-diagnosis devices using communication devices and a communication network is ongoing. As examples, methods of measuring biometric information using a communication device include: a method of including a measuring module, exclusive of a display, in the battery pack of a communication device; a method of minimizing a biometric information measuring module, attaching the minimized biometric information measuring module to a serial port, and performing measurement; and a method of transmitting data, measured by a portable health measuring device, to a remote health management server via a communication device using short-distance wireless communication.

However, the case of including a biometric information measuring module in a battery pack has a disadvantage in that high-temperature heat generated in the battery pack influences the measuring module and, thus, accurate measurement cannot be achieved. Furthermore, the method of minimizing a biometric information measuring module and attaching the minimized biometric information measuring module to a serial port has a disadvantage in that the minimization of the biometric information measuring module is limited in the case where the biometric information measuring module is equipped with all required components. Accordingly, there is a demand for the development of a device capable of managing health using a communication device directly or indirectly while maintaining the communication device in a light, thin, short and small form.

DISCLOSURE

Technical Problem

The present invention is intended to overcome the above-described problems of the conventional technologies, and an object of the present invention is to provide a foldable case-integrated multi-device, in which various sensors adapted to detect biometric information, which have not been dealt with due to the light, thin, short and small form of a communication device, are introduced into the foldable case of the communication device, thereby enabling a user to mount a desired sensor into a foldable case and easily perform health checking and management, and also enabling the sensor to be easily applied to the communication device.

Another object of the present invention is to provide a foldable case-integrated multi-device and a health management system using the same, in which a health care sensor is contained, so that health management can be performed, an environment contamination material, bacteria, or virus can be detected and, furthermore, the amount of exercise can be measured, thereby enabling comprehensive health management.

Technical Solution

In order to accomplish the above objects, in accordance with an aspect of the present invention, there is provided a foldable case-integrated multi-device including:

a foldable case including a case body configured to accommodate a communication device therein, a case cover, and a connection part configured to connect the case body and the case cover;

a sensor module contained in one side of the case cover, and configured to process measured biometric information;

a single-use multi-sensor configured to be detachably inserted into the sensor module, and to detect biometric information of a user; and flexible printed circuit boards (PCBs) mounted on the connection part, and configured to be connected to power of the communication device, to distribute the power to the sensor module, and to transmit data, processed by the sensor module, to the communication device.

In order to accomplish the above objects, in accordance with another aspect of the present invention, there is provided a health management system using a foldable case-integrated multi-device, the health management system including:

a foldable case-integrated multi-device including:
    a foldable case including a case body configured to
        accommodate a communication device therein, a case
        cover, and a connection part configured to connect the
        case body and the case cover;

a sensor module contained in one side of the case cover, and configured to process measured biometric information;

a single-use multi-sensor configured to be detachably inserted into the sensor module, and to detect biometric information of a user; and flexible printed circuit boards (PCBs) mounted on the connection part, and configured to be connected to power of the communication device, to distribute the power to the sensor module, and to transmit data, processed by the sensor module, to the communication device; and a communication device configured to receive the measured biometric information from the foldable case-integrated multi-device, to store the measured biometric information, to generate health management information or diagnostic data by processing the measured biometric information, and to display the health management information or diagnostic data.

According to another embodiment of the present invention, there is provided the foldable case-integrated multi-device, wherein the single-use multi-sensor sensor is a single-use electrochemical strip sensor including: a strip sensor; and an electrode unit including a plurality of electrodes configured to receive the sample from the strip sensor and generate current based on an electric potential difference.

Advantageous Effects

In the foldable case-integrated multi-devices according to various embodiments of the present invention, the sensor module configured to measure biometric information is contained in the foldable case and power supply, data processing and analysis, and display are implemented using internal components of the communication device, thereby providing a cutting-edge health care function while maintaining the communication device in a light, thin, short and small form.

In particular, the foldable case-integrated multi-devices can be used as practical means which are used to prevent diseases and perform a life management service because the multi-device for health care is integrated with the foldable case, and which can bring about a change in ubiquitous health care capable of implementing a health management-based society because mobile communication and a diagnostic device capable of checking on health and transmitting or managing data anytime and anywhere are converged.

Furthermore, according to the present invention, various sensors configured to detect biometric information can be detachably inserted into the foldable case of the communication device, and thus an advantage arises in which a user can mount a desired sensor into the foldable case and can easily perform health check and management.

According to the present invention, biometric information measured by the sensor integrated with the foldable case can be continuously stored and collected in the communication device and also analysis data can be generated, thereby providing the advantage of enabling the foldable case-integrated multi-devices to be utilized as personal daily health diaries. Furthermore, the biometric information can be transmitted to a medical institution via the communication device, previously measured biometric information and currently measured biometric information can be compared and analyzed, and an expert can propose the direction of health management based on the health state of each individual, thereby providing the advantage of enabling comprehensive management, including prevention and management.

BEST MODE

Preferred embodiments of the present invention will be described in detail with reference to the accompanying drawings. In the following description of the present invention, a detailed description of a related well-known technology or configuration will be omitted when it is determined that the detailed description may make the gist of the present invention unnecessarily obscure.

In the use of communication devices, cases having various shapes have been used for the purposes of protecting the communication devices and accommodating cards or the like. Conventional foldable cases have been responsible for the limited functions of simply protecting communication devices against impact or damage, accommodating various types of cards, and the like.

The foldable case-integrated multi-device of the present invention enables a multi-sensor device having various functions to be implemented in a foldable case connected to a communication device. The foldable case-integrated multi-device may be configured such that the case cover of the foldable case is unfolded, a single-use multi-sensor is taken out of a sensor module contained in the inner surface of the case cover, and then measurement is performed, or such that a single-use multi-sensor is taken out and used in the state in which the case cover is folded. The foldable case is configured to connect to the power and display units of the communication device.

In the present invention, the term "communication device" refers to any mobile communication terminal that provides the function of enabling communication and the Internet to be used. The communication device includes a mobile phone, a smartphone, a laptop computer, a tablet PC, a pocket size PC, a two-in-one PC in which a notebook computer function and a tablet PC function are integrated with each other, other mobile personal computers, etc., but is not limited thereto.

Figure 1:
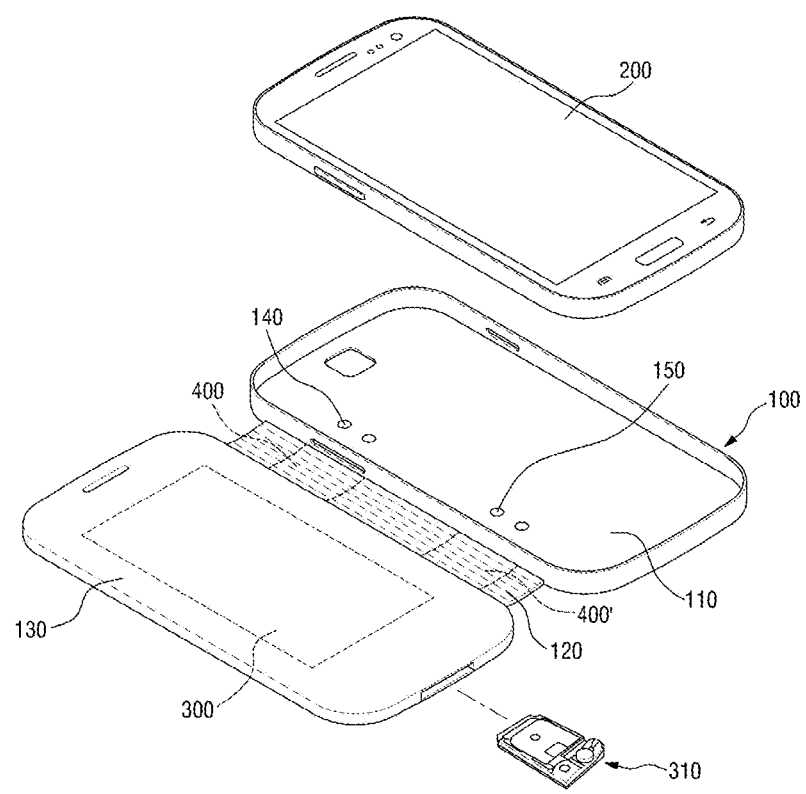
FIG. 1 is a schematic exploded perspective view of a foldable case-integrated multi-device according to an embodiment of the present invention.
Figure 2:
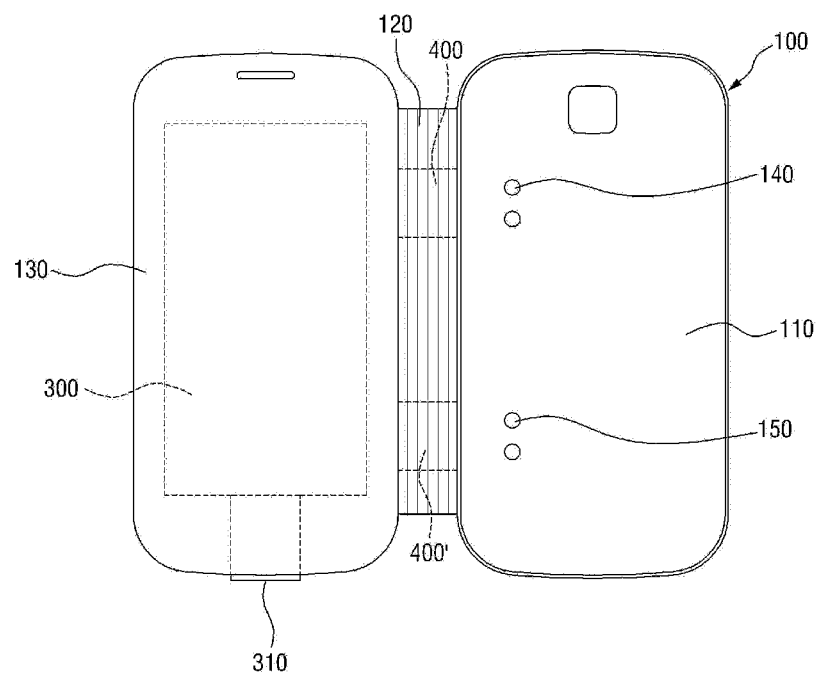
FIG. 2 is a rear view of a foldable case-integrated multi-device according to another embodiment of the present invention.

FIG. 1 is a schematic exploded perspective view of a foldable case-integrated multi-device, including a detachable sensor module, according to an embodiment of the present invention, and FIG. 2 is a rear view of a foldable case-integrated multi-device, including a back cover-integrated sensor module, according to another embodiment of the present invention.

Referring to FIG. 1, a foldable case-integrated multi-device according to an embodiment of the present invention includes: a foldable case 100 including a case body 110 configured to accommodate a communication device therein, a case cover 130, and a connection part 120 configured to connect the case body 110 and the case cover 130 in a foldable manner; a sensor module 300 contained in one side of the case cover 130, and configured to process measured biometric information; a single-use multi-sensor 310 configured to be detachably inserted into the sensor module 300, and to detect biometric information of a user; and flexible PCBs 400 and 400' mounted on the connection part 120, and configured to be connected to power of the communication device, to distribute the power to the sensor module 300, and to transmit data, processed by the sensor module 300, to the communication device 200. The flexible PCB 400 may be formed on a portion of the connection part 120 connected to power electrodes 140, and the flexible PCB 400' for data electrodes may be formed on a portion of the connection part 120 connected to the data connection portion 150.

The foldable case-integrated multi-device according to the embodiment of the present invention may include a single-use sensor or a Point of Care Testing (POCT) sensor in the sensor module 300, and may be configured to measure data when blood, saliva, urine or the like required for measurement is reacted and then inserted into and brought into contact with the sensor module 300 and to transmit the results of the measurement to the central processing unit 210 of the communication device 200.

A sensor is a device or a part for sensing or detecting a specific material, and includes a receptor configured such that various types of physicochemical reactions occur therein and a transducer configured to convert the reaction into an electric signal. The receptor employs a biomaterial. When the biomaterial recognizes a measurement target, a chemical change or a physical change occurs. A device for converting such a change into an electric signal is called a transducer, which is commonly called an electrode. Recent sensors have evolved into smarter devices that perform the processes of the recording, storage, transmission and feedback of information through the convergence of information processing technology and communication technology. The present invention is configured such that the sensors are configured in the form of thin films and introduced into the foldable case, so that the sensors can transmit a detected signal to the communication device 200 beyond the level of conventional sensors configured to simply detect a specific material and the central processing unit (CPU) 210 of the communication device can provide management service.

The foldable case 100 includes the case body 110 configured such that the communication device 200 is seated therein, the case cover 130 configured such that the sensor module 300 covering the front surface of the communication device is contained therein, and the connection part 120 configured to be connected to the case cover 130 in a folded state. The foldable case 100 may be implemented in various forms. For example, the foldable case 100 may be a detachable-type foldable case configured to fasten the overall device, a flip cover-type foldable case integrated with the back surface of the device, a view cover-type foldable case configured to allow a display part to be viewed therethrough, or the like according to a method of fastening the communication device.

The foldable case 100 is composed of a device including a plurality of layers more than one layer. The material of the foldable case may vary grip feeling by including plastic, artificial leather, non-woven fabric, or metal material. In the present invention, the foldable case 100 may be: a pouch-type case configured such that the communication device 200 is accommodated and stored in an accommodation space made of leather, fabric or the like; a wallet-type case configured such that artificial or synthetic leather is cut, a space adapted to accommodate the communication device therein is formed and a cover is formed to be selectively opened and closed; or a housing- or case-type case configured such that the communication device is inserted into and stored in an accommodation space inside synthetic resin, such as plastic, silicon or the like.

The single-use multi-sensor 310 capable of simultaneously performing various types of detection in the foldable case-integrated multi-device of the present invention is configured to be inserted into a side surface or one surface of the lower end of the case body 110 or a side surface or one surface of the lower end of the case cover 130 in which the sensor module 300 is contained. Although an example in which the single-use multi-sensor 310 is inserted longitudinally into the lower end of the case cover 130 is shown in FIGS. 1 and 2, the insertion of the single-use multi-sensor 310 is not necessarily limited thereto, but the single-use multi-sensor 310 may be configured to be inserted widthwise into the side surface of the case cover 130.

Figure 3:
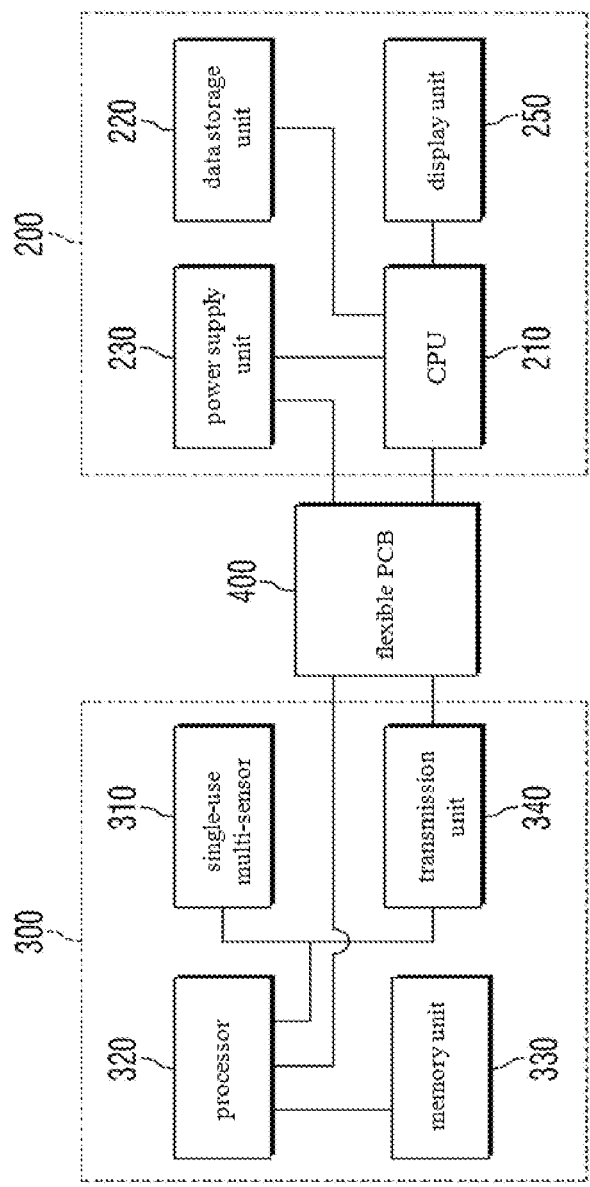
FIG. 3 is a block diagram of a health management system using a foldable case-integrated multi-device according to another embodiment of the present invention.

Referring to FIG. 3, in the present invention, the sensor module 300 may include: the single-use multi-sensor 310 configured to detect biometric information of a user; a processor 320 configured to control the operation of the single-use multi-sensor and process the detected biometric information; a memory unit 330 configured to store the data measured by the single-use multi-sensor 310; and a transmission unit 340 configured to transmit the data, processed by the processor 320, to the communication device 200 via the flexible PCB 400.

The processor 320 configured to process the measured data output from the sensor module 300 may be installed in foldable case 100, or may be installed in the communication device 200 in another embodiment.

The sensor module 300 may be configured to be selected from among an optical sensor, an electrochemical sensor, an electric conductivity sensor, and a chemosensor. A specific example of the sensor module 300 may be configured to include a combination of one or more sensors selected from among a blood sugar sensor, an environmental sensor, a Point of Care Testing (POCT) sensor, a pulse wave sensor, an oxygen saturation sensor, an electrocardiogram sensor, a cancer diagnosis sensor, a bioterrorism material sensor, a microbial sensor, a pregnancy test sensor, an anemia measurement sensor, an immunoassay sensor, a food sensor such as a sugar content sensor, a salinity sensor and an alcohol sensor, a strain sensor capable of measuring weight, a touch sensor, and an altitude sensor.

The optical sensor is based on a sensor using surface plasmon resonance, a colorimetric sensor using antigen-antibody reaction, or a fluorescence analysis sensor.

The electrochemical sensor may be classified as an electrochemical-type sensor, or as a sensor of a type using the electric conductivity of a nanowire. The electrochemical-type sensor measures a change in current, induced by an oxidation-reduction reaction occurring when a target material and a probe material are combined, using sensor electrodes. The sensor of a type using the electric conductivity of a nanowire is a non-label type sensor using the principle of detecting a change in electric conductivity inside a nanowire, which is induced by the charges of a biomaterial itself that is combined with the surface of the nanowire.

The chemosensor uses molecules that interact with energy or material and generate a measurable signal. The chemosensor detects a color, an absorption spectrum, a light emission spectrum, conductivity or the like, entailing a physical change, as a signal.

In the present invention, health management using a sensor is based on a concept different from that of management that is performed after a patient has received treatment, and refers to the process of performing fundamental control and management to prevent a patient from having a disease, i.e., the process of, even when health does not reach a level at which a disease occurs, performing patient monitoring or aged person monitoring and preventing a physical or emotional abnormal health state, such as obesity, stress or the like. For example, in the case of a human who is suspected to have diabetes, blood sugar levels may be periodically measured via a contained blood sugar sensor, and the blood sugar levels may be appropriately managed using an application of the communication device. Furthermore, not only the simple measurement of weight but also the measurement of metabolism, the percentage of body fat, and the mass ratio between muscles and bones may be taken using a smart scale for the management of weight.

In another example, the single-use multi-sensor 310 may be a sensor that detects a harmful factor that may cause a disease. This single-use multi-sensor 310 chiefly detects an environment contamination material, bacteria, or virus. For example, the single-use multi-sensor 310 may include a sensor capable of detecting a specific toxin that may cause food poisoning or the like or capable of detecting a causative germ that may cause avian influenza, or foot-and-mouth disease.

In still another example, when an exercise amount measuring device using a 3D accelerator sensor is employed, the amount of exercise of a user may be managed by accurately detecting a situation, such as walking, running, or walking up and down stairs, through the measurement of the amount of exercise and then calculating a more accurate measurement value.

Using the Point of Care Testing (POCT) sensor, specific protein or a specific toxin that may develop in blood when a heart attack occurs may be rapidly and simply identified via the collection of blood and then a patient may be diagnosed as a heart attack patient, or the numerical value of transaminase, such as glutamine oxaloacetic transaminase (GOT) or glutamine pyruvic transaminase (GPT), in blood may be measured using a minimum sample via a liver function test, an infectious disease test or the like.

In the present invention, both inorganic and organic samples may be used as the sample, used in the single-use multi-sensor 310, without limitations. Preferably, the sample used in the single-use multi-sensor 310 may be a bio sample, for example, blood, a body fluid, urine, saliva, or the like. Accordingly, the single-use multi-sensor 310 of the present invention may use the manufacturing protocol of conventional diagnosis kits without changes, and may be used as quantifiable various types of diagnosis kits for various application fields related to the analysis and/or diagnosis of samples, various diseases, and various samples. For example, the single-use multi-sensor 310 of the present invention may be applied to a biosensor, a DNA analysis chip, a protein analysis chip, a lab-on-a-chip, a cell counting device, an enzyme-linked immunosorbent assay (ELISA) sensor, etc.

In the present invention, an example of the single-use multi-sensor 310 is a sensor adapted to measure a substrate content in a sample liquid by using a biomaterial as a molecule identification element by means of the molecular recognition ability of the biomaterial, such as a microorganism, enzyme, an antibody, DNA, or RNA. That is, the sensor quantifies substrate included in the sample liquid using a reaction, for example, the consumption of oxygen attributable to the respiration of microorganisms, an enzyme reaction, light emission, or the like, occurring when the biomaterial recognizes a target substrate. Furthermore, among the various types of bio-sensors, an enzyme sensor may be an enzyme sensor that is a bio-sensor for, for example, glucose, a lactic acid, cholesterol, or an amino acid. This enzyme sensor is configured to perform the quantitative analysis of a sample in such a manner that an electron carrier is reduced by electrons generated via a reaction between a substrate included in, for example, a sample liquid i.e., a sample, and enzyme and an quantification device electrochemically measures the amount of reduction of the electron carrier.

Figure 4:
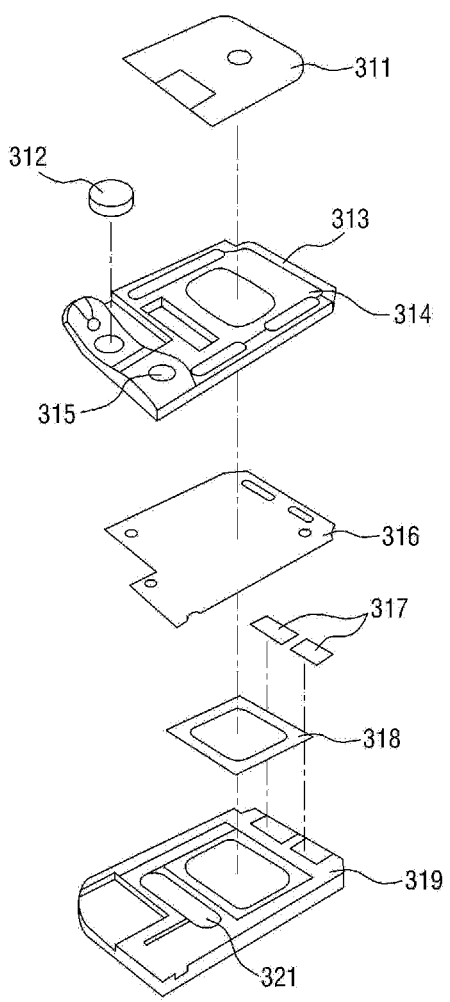
FIG. 4 is an exploded perspective view of the single-use multi-sensor of a foldable case-integrated multi-device according to an embodiment of the present invention.

An example of the single-use multi-sensor 310 which is available in the present invention is shown in FIG. 4. The single-use multi-sensor 310 may include a micro-fluidic biosensor chip that analyzes a small amount of body fluid, such as blood, saliva, urine or the like. As an example, the single-use multi-sensor 310 includes: a cartridge label 311; a sample feed gasket 312 configured to fasten a sample feed part 315; a fine sample flow path 313 formed in a narrow groove shape along the longitudinal direction of a surface of the sensor, formed to have a micro-liter level total volume into which a sample can be introduced and in which the sample is accommodated, and configured to sequentially guide the sample to the electrodes of the biosensor; a cartridge cover 314; the sample feed part 315 configured to introduce a test target sample; a film gasket 316; a biosensor chip 317; a sample accommodation part 318 configured to accommodate a sample; a cartridge base 319 configured such that an air vent connected to the sample feed part is formed and a depression adapted to accommodate the biosensor chip 317 is provided; and an air bladder 321 formed on the cartridge base 319 and provided with an air vent formed to be connected to the sample feed part 315. In this case, the device is configured to be disposed after single use or to be reused after chemical washing in order to protect an end user against exposure to biological waste in consideration of the communicability of the sample. The fine sample flow path 313 adapted to guide a sample is configured to enable the real-time monitoring of a disease using a micrometer unit of or a small volume of body fluid, and is configured to transfer a sample for a specific reaction by integrating various types of analysis in a single device.

Figure 5:
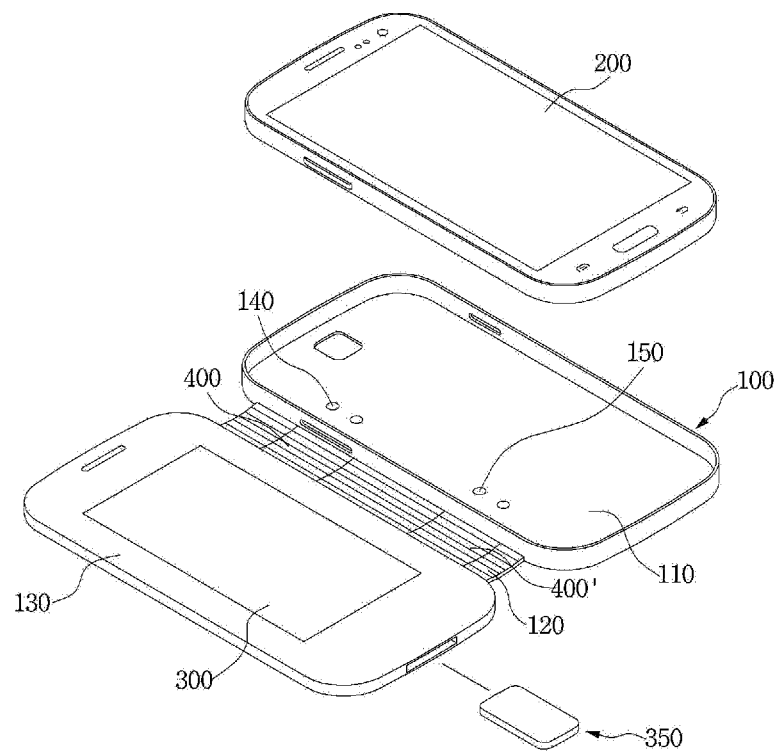
FIG. 5 is an exploded perspective view of a foldable case-integrated multi-device according to another embodiment of the present invention.

In another embodiment of the present invention, the single-use multi-sensor 310 may include a single-use electrochemical strip sensor 350, as shown in FIG. 5. The single-use strip sensor 350 receives power from the communication device 200, and transmits measured data to the central processing unit 210 of the communication device 200 via the flexible PCB 400.'

Another example of the sensor module 300 may be: an environment detection sensor, such as a carbon monoxide sensor, a formaldehyde sensor, a nitrogen dioxide sensor, an ozone sensor, a fine dust sensor, a bacteria detection sensor, an ultra-violet sensor, a Sox sensor, or an NOx sensor; a food sensor, such as a sugar content sensor, or a salinity sensor; a chemical sensor, such as an alcohol sensor, a hydrogen ion concentration sensor, or an agricultural pesticide detection sensor; a respiration sensor adapted to detect the breaking down of fats by detecting the amount of acetone broken down inside the body immediately after exercise; or an immunoassay sensor using an enzyme-linked immunosorbent Assay (ELISA).

The flexible PCB 400 is formed within the connection part 120, and is configured to be connected to the power supply unit 230 of the communication device 200. The foldable case-integrated multi-device receives power from the communication device 200 via the flexible PCB 400, and transmits measured data to the communication device 200, thereby managing the measured data. Referring to FIG. 5, the flexible PCB 400 of the smartphone case according to the embodiment of the present invention, the power electrodes 140 connected to the power supply unit 230 of the communication device, and the data connection portion 150 connected to the central processing unit 210 of the communication device are shown. As shown in FIG. 5, the power electrodes 140 and the data connection portion 150 for the communication device are configured to be electrically connected to the flexible PCBs 400 and 400' of the foldable case.

Figure 6:
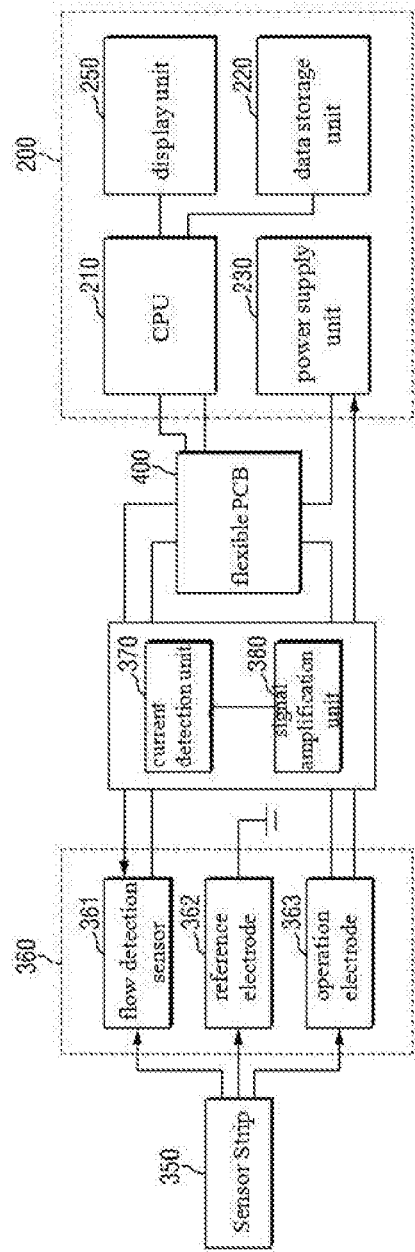
FIG. 6 is a block diagram of a health management system using a foldable case-integrated multi-device according to another embodiment of the present invention.
Figure 7:
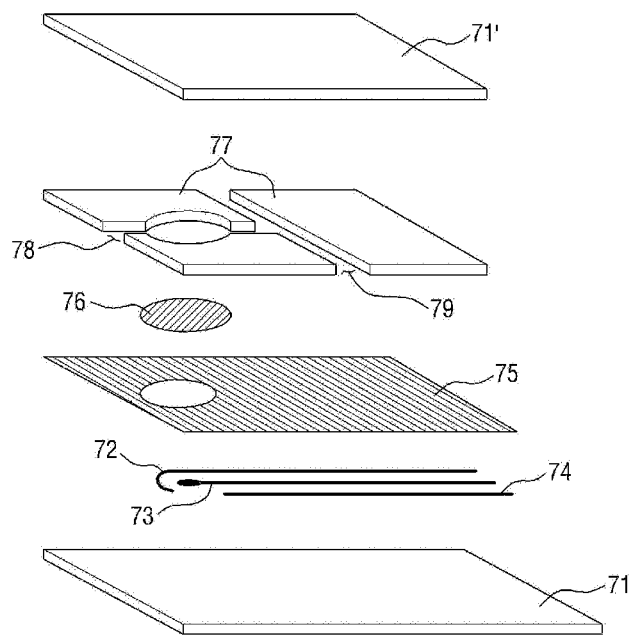
FIG. 7 is an exploded perspective view of the strip sensor of a foldable case-integrated multi-device according to another embodiment of the present invention.

FIG. 6 is a block diagram of a health management system including a strip sensor according to another embodiment of the present invention, and FIG. 7 is an exploded perspective view of the strip sensor. As shown in FIG. 6, the sensor module according to the other embodiment of the present invention includes a single-use strip sensor 350, an electrode unit 360, a signal amplification unit 370, and a signal processing unit 380. The single-use strip sensor 350 collects and feeds a sample, such as blood, urine, expiratory breath, or the like.

The electrode unit 360 includes a plurality of electrodes 361, 362 and 363 that receive a sample from the single-use strip sensor 350 and generate current based on an electric potential difference. The electrode unit 360 may include: a flow detection electrode 361 configured to receive sample blood and generate a first electric potential value; a reference electrode 362 configured to function as a ground function; and an operation electrode 363 configured to receive the sample and generate a second electric potential value.

The signal amplification unit 370 detects and amplifies an electric signal detected by the electrode unit 360, and the signal processing unit 380 receives the amplified electric signal, calculates a measured biometric information value, and transmits the measured biometric information value to the communication device 200 via the flexible PCB 400.'

FIG. 7 is an exploded perspective view showing an example of the single-use strip sensor 350. Referring to FIG. 7, in the strip sensor, a flow detection electrode 72, an operation electrode 73 and a reference electrode 74 are disposed on a lower substrate 71, an insulation plate 75 configured such that a portion corresponding to the flow detection electrode 72 and the operation electrode 73 is cut out, thereby defining a reaction region, is disposed on the electrodes 72, 73 and 74, and a buffer layer 76 configured to include electron transfer media disposed at locations corresponding to the operation electrode 73 and the flow detection electrode 72 and formed in the operation electrode and the flow detection electrode, a double-sided adhesive tape 77 configured to adhere an upper substrate 71' and an insulation layer, and the upper substrate 71' are sequentially disposed on the buffer layer 76. A sample inlet 78 is formed at the location of the double-sided adhesive tape 77 corresponding to the flow detection electrode and the operation electrode, and an air vent 79 configured to discharge air is formed in a portion of the double-sided adhesive tape 77.

The lower substrate 71 is made of ceramic, a glass plate or an insulation polymer film like the upper substrate 71,' and is combined with the upper substrate 71' to thus form a housing. The polymer material is preferably an organic polymer material, such as polyester, polyvinylchloride, polycarbonate or the like.

More specifically, the electrode unit 360 is configured to include the operation electrode 363 and the reference electrode 362, and may measure the accurate concentration of a biological sample using electric conductivity that is measured by applying an alternating current (AC) at 1 or higher kHz.

In the present invention, the material of the electrodes is not specially limited as long as the material is a conductive material. Examples of the conductive material include silver, palladium, copper, gold, platinum, iridium, silver/silver chloride, carbon paste, etc. The operation electrode 73 and the reference electrode 74 may be formed by performing the screen printing, physical vapor deposition or etching of a conductive material on a substrate, the attachment of a conductor tape, inkjet printing, or the like.

The insulation plate 75 is responsible for the function of minimizing measurement error by maximally making the area of the operation electrode 73 and the reference electrode 74, exposed to a test sample, uniform and also maintaining the distance between the electrodes at a constant value.

An example of the single-use strip sensor 350 may be a blood sugar measuring biosensor. In the case of the blood sugar measuring biosensor, a predetermined electrode is formed, and then a reaction layer is formed by fixing a blood glucose oxidase, i.e., an analytic reagent, on part of the electrode. When a sample is introduced into the reaction layer, blood glucose in blood is oxidized by the blood glucose oxidase, and the blood glucose oxidase is reduced. An electron accepter oxidizes the blood glucose oxidase, and is reduced. The reduced electron accepter loses electrons on the surface of the electrode onto which a predetermined voltage is applied, and is electrochemically oxidized again. The concentration of glucose in the sample is proportional to the amount of current generated during the oxidization of the electron accepter, and thus the concentration of blood glucose may be measured by measuring the amount of current.

Meanwhile, although the foldable case-integrated multi-device of the present invention may transmit measured data to the central processing unit 210 of the communication device 200 via the flexible PCB 400, it may additionally include a wireless communication unit (not shown), such as a ZigBee module or a Bluetooth module, as an alternative. In this embodiment, the sensor modules 300 installed in the foldable case may transmit biometric information to the central processing unit 210 of the communication device 200 via wireless communication.

According to the foldable case-integrated multi-device of the present invention, biometric information measured by the sensor module in single measurement is transmitted to the communication device which can freely perform data transmission and reception over a wireless communication network and includes a desirable OS and a processor capable of performing high-performance computation, so that a user's own biometric information is continuously stored in the communication device itself and thus effective biometric information acquired in his or her daily life can be utilized as basic data for health management, and so that his or her own health state can be immediately determined and thus attention can be called in his or her real life.

Another implementation of the present invention is directed to a health management system using a foldable case-integrated multi-device, the health management system including:

a foldable case-integrated multi-device, including: a foldable case including a case body configured to accommodate a communication device therein, a case cover, and a connection part configured to connect the case body 110 and the case cover; a sensor module contained in one side of the case cover, and configured to process measured biometric information; a single-use multi-sensor configured to be detachably inserted into the sensor module and to detect biometric information of a user; and flexible printed circuit boards (PCBs) mounted on the connection part, and configured to be connected to power of the communication device, to distribute the power to the sensor module, and to transmit data, processed by the sensor module, to the communication device; and a communication device configured to receive the measured biometric information from the foldable case-integrated multi-device, to store the measured biometric information, to generate health management information or diagnostic data by processing the measured biometric information, and to display the health management information or diagnostic data.

Referring to FIG. 3, the sensor module 300 installed in the foldable case 100 measures various types of data including biometric information, and transmits the measured data including biometric information to the central processing unit 210 of the communication device via the flexible PCB 400' for data electrodes and the data connection portion 150 for the communication device 200. In this case, the central processing unit 210 of the communication device may process the biometric information data, and may display the results of the processing on the display unit 250 of the communication device.

In the present invention, the sensor module 300 for the measurement of biometric information is mounted in the foldable case 100, and corresponding internal components of the communication device 200 are used as the power supply unit 230, an analog-digital converter (ADC), and the control unit. That is, a corresponding component of the communication device is used as the analog-digital converter configured to convert a measured analog signal into a digital signal in order to construct the sensor module in the form of a thin film, and the central processing unit 210 of the communication device 200 may be used as the control unit configured to process the digital signal obtained through the conversion.

The display unit 250 displays the biometric information measured by the sensor module 300 so that a user can view the biometric information. The display unit 250 may display the biometric information measured by the sensor module 300 of the foldable case not only in the form of simple numerical values but also in a form to which various graphic effects are added, thereby enabling a user to visually, more rapidly and easily view and interpret the biometric information. In this case, the display unit 250 may display not only current biometric information but also past biometric information, thereby enabling a user to visually and easily view changes in his or her biometric information for a predetermined period.

The communication device 200 may be configured to store the received biometric information of a user together with additional identification information, such as the date and time of measurement, in the data storage unit 220 provided in the communication device. As described above, the communication device 200 continuously stores the biometric information of a user and changes in biometric information may be easily checked on via the display unit 250 later, and thus the biometric information measured by the sensor module 300 of the foldable case may be used as basic data that is used to manage and diagnose a health state for each individual.

The central processing unit 210 is configured to control various types of signal processing related to the biometric information, such as the reception of the biometric information from the sensor module 300, the storage of the biometric information, and the processing of the measured data, which are performed in the communication device 200. Furthermore, the central processing unit 210 of the communication device 200 is configured to generate diagnostic data that is used to determine and diagnose a current health state by comparing biometric information recently acquired by the sensor module 300 with past biometric information stored in the data storage unit 220. Furthermore, whether medical measures are required to be taken is determined by comparing the value of the actual biometric information of each user measured by the sensor module 300 with the value of average biometric information and the value of medically recommended biometric information, and the result of the comparing may be fed back to the user. For example, the central processing unit 210 may further include a determination unit that transmits an alarm message to the display unit when a measured value is out of an allowable range.

Accordingly, according to the health management system of the present invention, biometric information may be measured only in such a way that a user inserts only a required sensor into the foldable case and that software or an application required to perform the health management process has been already installed in the communication device or the user accesses the wireless Internet and downloads software or an application. Accordingly, health management, exercise management, environment management, food management, etc. may be easily and inexpensively performed any time and any place.

Figure 8:
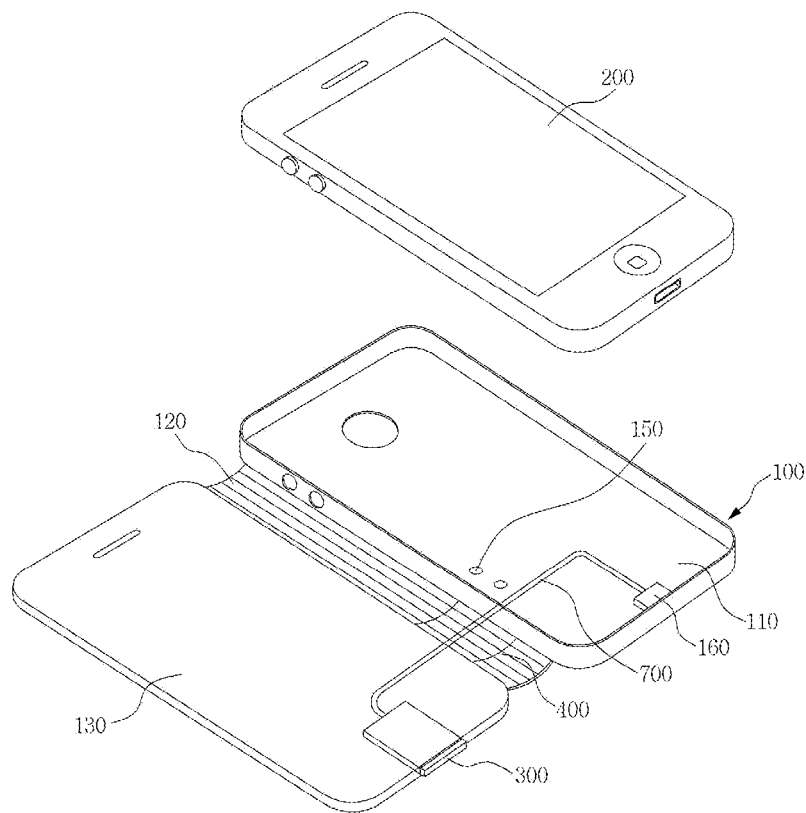
FIG. 8 is a schematic perspective view of a foldable case-integrated multi-device according to still another embodiment of the present invention.

Depending on the model of a communication device, there is a model in which a battery cannot be separated from a communication device because the battery is integrated with the communication device. FIG. 8 is a schematic perspective view of a foldable case-integrated multi-device according to still another embodiment of the present invention. As shown in FIG. 8, the communication device is configured such that a power supply line and a data line 700 are extended from an inner power terminal 160 inside a case body 110, are passed through the case body 110 and a flexible PCB 400, and are connected to the sensor module 300.

It will be apparent to those having ordinary knowledge in the art to which the present invention pertains that various modifications and alternations may be made within a range that does not depart from the essential features of the present invention. Accordingly, the embodiments disclosed in the present specification are not intended to limit the technical spirit but are intended to illustrate the present invention, and the range of the technical sprit of the present invention is not

The invention claimed is:

1. A foldable case-integrated multi-device, comprising:
a foldable case including a case body configured to accommodate a communication device therein, a case cover, and a foldable connection part configured to connect the case body and the case cover;
a detachable sensor module contained in one side of the case cover;
a multi-sensor configured to be detachably inserted into the detachable sensor module;
the multi-sensor including a biosensor chip configured to detect biometric information of a user;
the detachable sensor module including a processor configured to process the biometric information and measure the biometric information; and
flexible printed circuit boards (PCBs) mounted on the connection part, and configured to connect to power of the communication device, to distribute the power to the detachable sensor module, and to transmit data, processed by the processor of the detachable sensor module, to the communication device,
wherein the flexible PCBs are formed within the foldable connection part, and are configured to connect to power electrodes and a data connection portion for the communication device, and
wherein the multi-sensor includes:
a sample feed gasket configured to fasten a sample feed part;
a fine sample flow path formed in a narrow groove shape along a longitudinal direction of a surface of the multi-sensor, configured to sequentially guide a sample to electrodes of the biosensor chip;
a cartridge cover;
the sample feed part configured to introduce a test sample;
the biosensor chip;
a sample accommodation part configured to accommodate the sample;
a cartridge base configured such that a depression adapted to accommodate the biosensor chip is provided.

2. The foldable case-integrated multi-device of claim 1, wherein the sensor module comprises:
the processor configured to control operation of the multi-sensor;
a memory unit configured to store as data the biometric information detected by the multi-sensor; and
a transmission unit configured to transmit the biometric information processed by the processor to the communication device via the flexible PCB.

3. The foldable case-integrated multi-device of claim 1, wherein the sensor module is one or more selected from the group consisting of a blood sugar sensor, a respiratory sensor, an obesity sensor, an environmental sensor, a Point of Care Testing (POCT) sensor, a three-dimensional acceleration sensor, a pulse wave sensor, an oxygen saturation sensor, an electrocardiogram sensor, a cancer diagnosis sensor, a bioterrorism material sensor, a microbial sensor, a pregnancy test sensor, an anemia measurement sensor, an immunoassay sensor, a sugar content sensor, a salinity sensor, an alcohol sensor, a weight sensor, a touch sensor, and an altitude sensor.

4. The foldable case-integrated multi-device of claim 1, wherein the sensor module is one of an optical sensor, an electrochemical sensor, an electric conductivity sensor, and a chemosensor.

5. The foldable case-integrated multi-device of claim 1, wherein the case body includes a plurality of layers more than one layer.

6. The foldable case-integrated multi-device of claim 1, wherein the case is made of one of plastic, artificial leather, non-woven fabric, and a metallic substrate.

7. The foldable case-integrated multi-device of claim 1, wherein the foldable case is one of an insertion-type case, a flip cover-type case, and a view cover-type case.

8. The foldable case-integrated multi-device of claim 1, wherein the sensor module includes one or more bio-chips selected from the group consisting of a DNA analysis chip, a protein analysis chip, and a lab-on-a-chip.

9. The foldable case-integrated multi-device of claim 8, wherein the bio-chips include a micro-fluidic biosensor chip.

10. The foldable case-integrated multi-device of claim 1, wherein the sensor module is a back cover-integrated sensor module.

11. A health management system using a foldable case-integrated multi-device, the health management system comprising:
the foldable case-integrated multi-device according to claim 1; and
a communication device configured to receive the biometric information from the foldable case-integrated multi-device, to store the biometric information, to generate health management information or diagnostic data by processing the biometric information, and to display the health management information or diagnostic data.

12. The health management system of claim 11, further comprising a power supply line and a data line that extend from an inner power terminal of the communication device to the flexible PCBs.

13. The foldable case-integrated multi-device of claim 1, wherein the multi-sensor further includes:
a cartridge label;
a film gasket; and
an air bladder formed on the cartridge base and provided with an air vent connected to the sample feed part.

14. A foldable case-integrated multi-device, comprising:
a foldable case including a case body configured to accommodate a communication device therein, a case cover, and a connection part configured to connect the case body and the case cover;
a sensor module contained in one side of the case cover, and configured to process measured biometric information;
a single-use multi-sensor configured to be detachably inserted into the sensor module, and to detect biometric information of a user; and
flexible printed circuit boards (PCBs) mounted on the connection part, and configured to connect to power of the communication device, to distribute the power to the sensor module, and to transmit data, processed by the sensor module, to the communication device,
wherein the single-use multi-sensor includes:
a cartridge label;
a sample feed gasket configured to fasten a sample feed part;
a fine sample flow path formed in a narrow groove shape along a longitudinal direction of a surface of the sensor, formed to have a micro-liter level total volume into which a sample can be introduced and in which the sample can be accommodated, and configured to sequentially guide the sample to electrodes of the biosensor;

a cartridge cover;

the sample feed part configured to introduce a test target sample;

a film gasket;

a biosensor chip;

a sample accommodation part configured to accommodate a sample;

a cartridge base configured such that an air vent connected to the sample feed part is formed and a depression adapted to accommodate the biosensor chip is provided; and an air bladder formed on the cartridge base and provided with an air vent connected to the sample feed part.

* * * * *